United States Patent [19]
Washburn et al.

[11] Patent Number: 6,162,176
[45] Date of Patent: Dec. 19, 2000

[54] ULTRASOUND COLOR FLOW DISPLAY OPTIMIZATION

[75] Inventors: Michael J. Washburn, New Berlin; Gary E. MacLeod, Menomonee Falls; Sean D. Lucas, Waukesha; David J. Muzilla, Mukwonago, all of Wis.

[73] Assignee: General Electric Company, Milwaukee, Wis.

[21] Appl. No.: 09/224,634

[22] Filed: Dec. 31, 1998

[51] Int. Cl.⁷ .................................................... A61B 8/12
[52] U.S. Cl. ............................................................ 600/454
[58] Field of Search ................................ 600/443, 447, 600/453, 454–456

[56] References Cited

U.S. PATENT DOCUMENTS

| 5,246,006 | 9/1993 | Kanda et al. . | |
| 5,404,883 | 4/1995 | Freedman et al. | 600/443 |
| 5,720,288 | 2/1998 | Liu | 600/443 |
| 5,735,797 | 4/1998 | Muzilla et al. . | |
| 6,017,309 | 1/2000 | Wasburn et al. | 600/454 |
| 6,050,942 | 4/2000 | Rust et al. | 600/437 |

FOREIGN PATENT DOCUMENTS

| 0 830 842 A1 | 3/1998 | European Pat. Off. . |
| 0 843 181 A1 | 5/1998 | European Pat. Off. . |
| 0 871 043 A2 | 10/1998 | European Pat. Off. . |
| 0 952 458 A2 | 10/1999 | European Pat. Off. . |

*Primary Examiner*—Marvin M. Lateef
*Assistant Examiner*—Ali M. Imam
*Attorney, Agent, or Firm*—McAndrews, Held & Malloy; Christian G. Cabou; Phyllis Y. Price

[57] ABSTRACT

An ultrasound color flow imaging system is programmed to optimize display images of power and velocity by automatically adjusting thresholds and data compression by using histograms and samplings of color flow data.

40 Claims, 6 Drawing Sheets

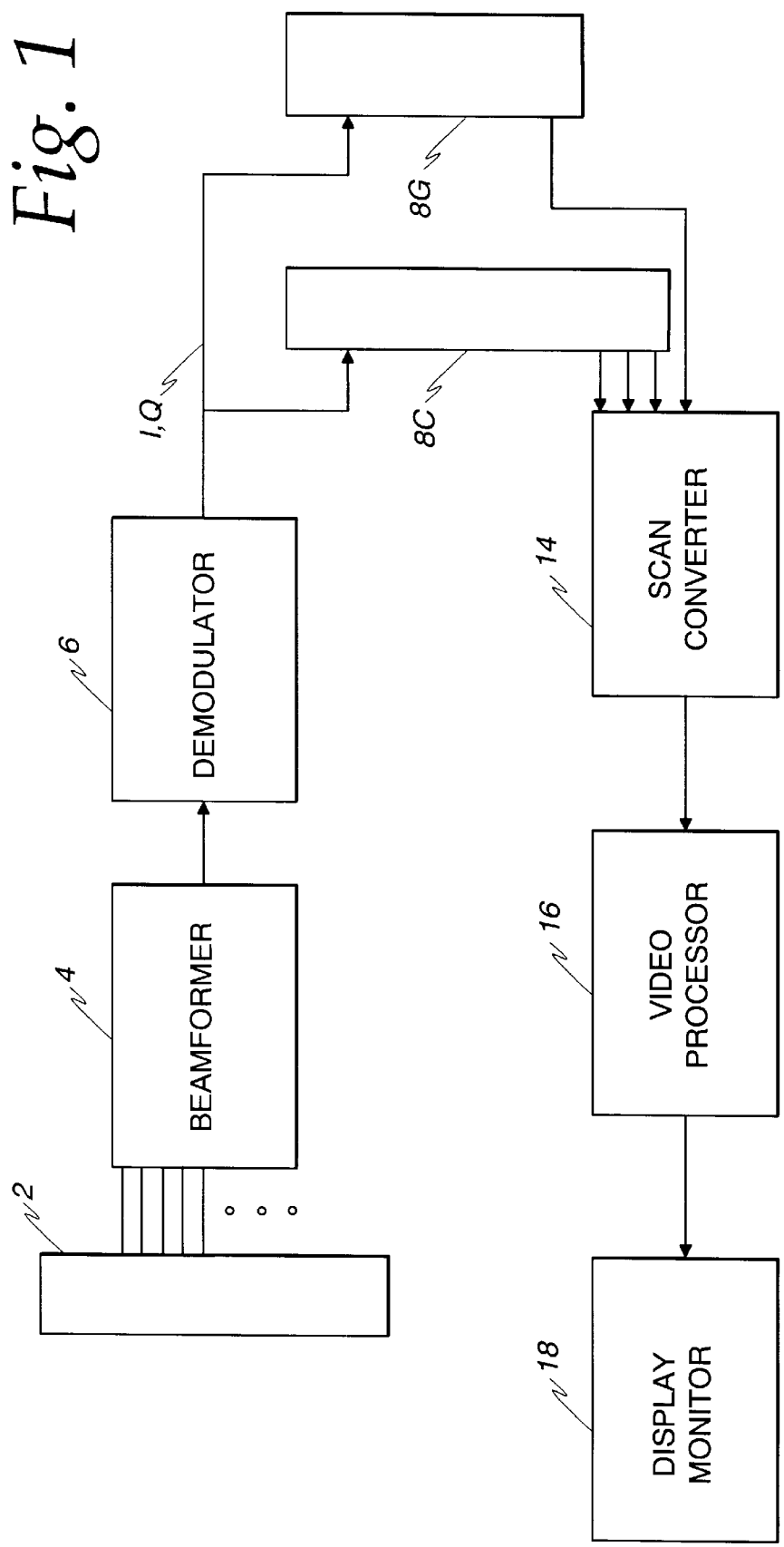

ULTRASOUND COLOR FLOW DISPLAY OPTIMIZATION

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention generally relates to ultrasound color flow Doppler imaging of fluid flow fields. In particular, the invention relates to a method and an apparatus for improving the display of such imaging.

Ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency, i.e., phase shift, translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, color flow mode displays hundreds of adjacent sample volumes simultaneously, all laid over a B-mode image and color-coded to represent each sample volume's velocity.

Typically, color flow processors estimate blood flow velocity, blood flow power, and blood flow variance. Typically, color flow data is used to modify the color of a region of interest on a display screen. The user selects the type of data used for the display. The modes typically available are power only, velocity only or velocity and variance combined.

In current ultrasound scanners, various color flow display parameters are either fixed with no user selectability or are preset to some specific setting and can only be changed if action is taken by the user, one parameter at a time. This limits image quality and user productivity for any given application and scanning situation. There is a need for a scanner in which these same parameters can all be automatically adjusted at the same time to optimize image quality related to color flow display for a specific scanning situation, thus increasing user productivity.

In the color flow power mode of operation, known ultrasound scanners typically provide a color flow dynamic range based on a compression curve preselected at the factory depending on the type of scanning application. For example, one dynamic range based on one compression curve is selected for scanning of the kidney, whereas another dynamic range based on another compression curve is selected for scanning of the carotid artery. Frequently, the actual scan data has a dynamic range different from the range upon which the compression curve is based. As a result, the dynamic range of the display is less than optimal.

Accordingly, there is a need for a color flow ultrasound scanner which can automatically adjust for changes in the dynamic range of the received signals.

In the color flow power or color flow velocity modes of operation, known ultrasound scanners provide a B/color priority threshold which is user selectable from a softkey menu on the user's console of the scanner. The threshold may be set by the user to various percentages of the maximum B-mode gray scale value. For any pixel within the color mode region of interest (ROI), if the B-mode pixel value exceeds the selected B/color priority threshold, then the B-mode value is displayed for that pixel. Otherwise, the corresponding color pixel value is displayed, if there is one. However, the actual B-mode data maximum value may vary over a wide range. As a result, the threshold is frequently less than optimal. Accordingly, there is a need for a color flow ultrasound scanner which can automatically adjust the B/color priority threshold according to the actual B-mode data.

In the color flow power or color flow velocity modes of operation, known ultrasound scanners provide user selectable color maps that are applied to the color mode data. In the power mode, the possible data values are 7-bits (0–127). In the velocity mode, the data values are signed 7-bits (−128 to +127). In a known system, any given map is fixed with the colors in the map being applied across the range of data values for power or velocity modes. There are also fixed map thresholds which are set such that color data will be displayed if it is above this threshold and will not be displayed if it is below this threshold. Such thresholding typically is used to minimize unwanted noise and artifacts. There are many scanning situations, however, where the color data in the ROI does not extend over the full possible range of output values, and therefore, many colors in the map are not used on the data which is present in the ROI. Also, the fixed map threshold may be too high for some scanning situations, causing low flow to be thresholded out even if no artifacts are present. As a result, there is a need for a color flow system in which the map and map threshold an be adjusted automatically.

BRIEF SUMMARY OF THE INVENTION

One aspect of the invention is useful in an ultrasound imaging system generating color flow signals in response to ultrasound signals backscattered from a subject under study. This aspect of the invention displays images in response to the color flow signals by storing first memory values in response to the color flow signals, preferably in a digital memory. A dynamic range compression scheme is determined based on an analysis of the first memory values, preferably by a logic unit. Second memory values are generated based on the dynamic range compression scheme and a color flow image is displayed in response to the second memory values, preferably by a color display unit.

Another aspect of the invention is useful in an ultrasound imaging system generating color flow signals in response to ultrasound signals backscattered from a subject under study and generating image signals based on the amplitude of ultrasound signals backscattered from the subject under study. This aspect of the invention displays images in response to the color flow signals by receiving a threshold signal preferably from a user operated control. A first set of data words is stored in response to the color flow signals and a second set of data words is stored in response to the image signals preferably in a digital memory. A characteristic value corresponding to at least one characteristic of the second set of data words is determined, preferably by a logic unit. The threshold value is altered in response to the characteristic value. Data words are selected from the first and second sets depending on a predetermined relationship between the altered threshold value and the values of the data words in the first and second sets, preferably by the logic unit. A color flow image is displayed in response to the selected data words.

Another aspect of the invention is useful in an ultrasound imaging system generating color flow signals in response to ultrasound signals backscattered from a subject under study and generating image signals based on the amplitude of ultrasound signals backscattered from the subject under study. This aspect of the invention displays images in response to the color flow signals by receiving a threshold signal preferably from a user operated control. A first set of data words is stored in response to the color flow signals, and a second set of data words is stored in response to the image signals, preferably by a digital memory. The threshold signal is adjusted to a first threshold value. Samples of the second set of data words are analyzed to determine an initial count of data words having a first predetermined relationship with respect to the first threshold value, preferably by a logic unit. The threshold signal is adjusted to one or more additional threshold values, preferably by the logic unit. The second data words are sampled one or more additional times until the number of second set data words having the first predetermined relationship with respect to the additional threshold values reaches a target count having a second predetermined relationship with respect to the initial count and corresponding to a target threshold value. Data words are selected from the first and second sets depending on a third predetermined relationship between the target threshold value and the values of the data words in the first and second sets, preferably by the logic unit. A color flow image is displayed in response to the selected data words.

Another aspect of the invention is useful in an ultrasound imaging system generating color flow signals in response to ultrasound signals backscattered from a subject under study. This aspect of the invention displays images in response to the color flow signals by receiving a threshold signal, preferably at a terminal from a memory. Data words are stored in response to the color flow signals, preferably in a digital memory. The value of the threshold signal is altered based on an analysis of the data words, preferably by a logic unit. Data words are selected from the memory depending on a predetermined relationship between the altered threshold value and the values of the data words, preferably by a logic unit. A color flow image is displayed in response to the selected data words, preferably by a color display unit.

Color flow image display can be improved by combining the foregoing aspects of the invention. For example, a first threshold signal having a first threshold value is received, and a second threshold signal having a second threshold value also is received, preferably at a terminal from storage. A first set of data words is stored in response to the color flow signals and a second set of data words is stored in response to the image signals; preferably by a digital memory. A dynamic range compression scheme is determined by analyzing the data words in the first set. The data words are altered in the first set based on the determined dynamic range compression scheme. The second threshold value is altered based on an analysis of the first set of data words. A characteristic value corresponding to at least one characteristic of the second set of data words is determined. The first threshold value is altered in response to the characteristic value. Data words from the first and second sets are selected depending on a first predetermined relationship between the altered first threshold value and altered second threshold value and the values of the data words in the first and second sets. The foregoing determining, analyzing and altering preferably are carried out by a logic unit, such as a digital signal processor.

A color flow image is displayed in response to the selected data words, preferably by a display unit.

By using the forgoing techniques, the color flow display of an ultrasound imaging device can be automatically adjusted for optimum viewing.

BRIEF DESCRIPTION OF THE DRAWINGS

FIG. 1 is a schematic block diagram showing the signal processing chain for a conventional color flow and B-mode ultrasound imaging system.

DETAILED DESCRIPTION OF THE INVENTION

Referring to FIG. 1, the basic signal processing chain for a color flow and gray scale imaging system comprises an ultrasound transducer array 2, which is activated to transmit pulse sequences comprising tone bursts of length P which are fired repeatedly at a pulse repetition frequency (PRF) which typically is in the kilohertz range. The pulse sequences, including burst lengths P, are different for the color flow and B-mode processing. For color flow imaging, P may be 4 to 8 cycles, and the tone bursts are focused at the same transmit focal position with the same transmit characteristics.

A series of color flow transmit firings focused at the same transmit focal position are referred to as a "packet". Each transmit beam propagates through the object being scanned and is reflected by ultrasound scatterers in the object.

The return RF signals are detected by the transducer elements and received by the respective receive channels in the beamformer 4. The beamformer sums the delayed channel data and outputs in a beam summed signal which is demodulated into in-phase and quadrature (I/Q) signal components by a demodulator 6. The B-mode I, Q outputs from demodulator 6 are transmitted to a mid processor 8G for gray scale B-mode processing, and the color flow I, Q outputs from demodulator 6 are transmitted to a midprocessor 8C for color processing.

Figure 2:
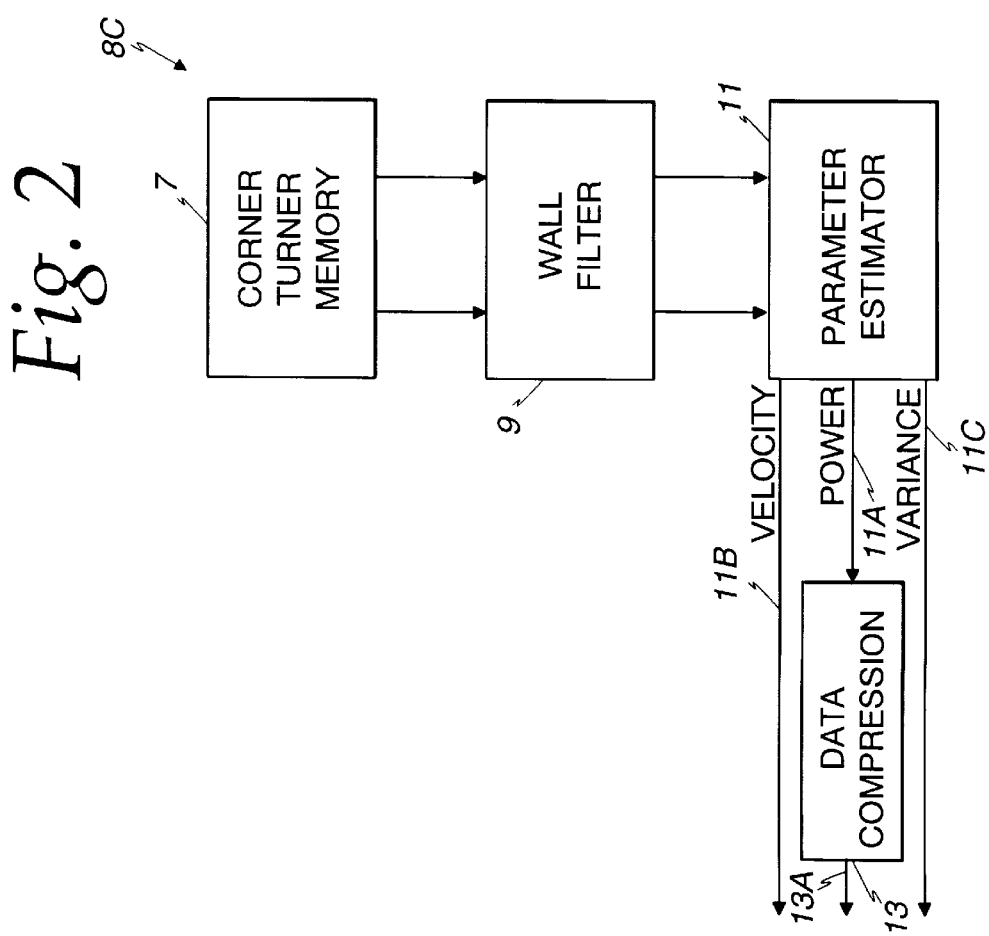
FIG. 2 is a schematic block diagram showing the mid processor color flow apparatus illustrated in FIG. 1.

FIG. 2 illustrates mid-processor 8C. The I/Q signal components from demodulator 6 are stored in a corner turner memory 7, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through a wall filter 9 which rejects any clutter corresponding to stationary or very slow-moving tissue. The filtered outputs are then fed into a parameter estimator 11, which converts the range cell information into the intermediate autocorrelation parameters N, D and R(O). N and D are the numerator and denominator for the autocorrelation equation, as shown below:

$$N = \sum_{i=1}^{M-1} (I_i Q_{i+1} - I_{i+1} Q_i) \qquad (2)$$

$$D = \sum_{i=1}^{M-1} (I_i I_{i+1} + Q_i Q_{i+1}) \qquad (3)$$

where $I_i$ and $Q_i$ are the demodulated, basebanded input data for firing i, and M is the number of firings in the packet. R(O) is approximated as a finite sum over the number of firings in a packet, as follows:

$$R(O) = \sum_{i=1}^{M-1} \frac{(I_i^2 + Q_i^2 + I_{i+1}^2 + Q_{i+1}^2)}{2} \qquad (4)$$

A processor converts N and D into a magnitude and phase for each range cell. The equations used are as follows:

$$|R(T)| = \sqrt{N^2 + D^2} \qquad (5)$$

$$\phi(R(T)) = \tan^{-1}\left[\frac{N}{D}\right] \qquad (6)$$

The parameter estimator processes the magnitude and phase values into signals having values representing estimates of power, velocity and turbulence or variance which are transmitted on conductors 11A, and 11B and 11C, respectively. The phase is used to calculate the mean Doppler frequency, which is proportional to the velocity as shown below; R(O) and |R(T)|(magnitude) are used to estimate the turbulence.

The mean Doppler frequency in hertz is obtained from the phase of N and D and the pulse repetition from T:

$$\overline{f} = \frac{1}{2\pi T}\tan^{-1}\left[\frac{N}{D}\right] = \frac{1}{2\pi T}(\phi(R(T))) \qquad (7)$$

The mean velocity is calculated using the Doppler shift equation below. Since θ, the angle between the flow direction and the sampling direction, is not known, cos θ is assumed to be 1.0.

$$\overline{v} = \frac{\overline{f}}{f_o}\frac{c}{2\cos\theta}$$

Preferably, the parameter estimator does not calculate the mean Doppler frequency as an intermediate output, but calculates v directly from the phase output of the processor using a look-up table.

The turbulence may be calculated in the time domain as a second-order series expansion of the variance of the mean Doppler frequency. The time domain expression for turbulence involves calculating the zero-lag and one-lag autocorrelation functions, R(O) and R(T) respectively. The exact autocorrelation functions are approximated by finite sums over the known data in the number of firings in a packet:

$$\sigma^2 = \frac{2}{(2\pi T)^2}\left[1 - \frac{|R(T)|}{R(O)}\right] \qquad (9)$$

The mean value signal θ (R(T)) is an estimate of the mean Doppler frequency shift of the flowing reflectors, which in turn is proportional to the mean blood flow velocity. The variance signal $\sigma^2$ indicates the frequency spread of the flow signal component of the baseband echo signal. This value is indicative of flow turbulence, since laminar flow has a very narrow range of velocities, while turbulent flow is a mixture of many velocities. To indicate the strength of the signal from the flowing reflectors, the signal R(O) indicates the amount of the returned power in the Doppler-shifted flow signal.

The signal power on conductor 11A is passed through a data compression module 13 which compresses the data according to families of data compression curves. A different family of curves can be provided for different scanning applications. For example, one family of curves is provided for renal scanning, while another family of curves is provided for carotid artery scanning. Typically, there are about three curves per family. The dynamic range of the signals is changed according to the curve used for the data compression. The curves in each family are arranged in order of increasing dynamic range. Controller 26 sets the default curve when a user selects the scan application. The dynamic range controls the range of intensities or lumens created on display 18.

Figure 3:
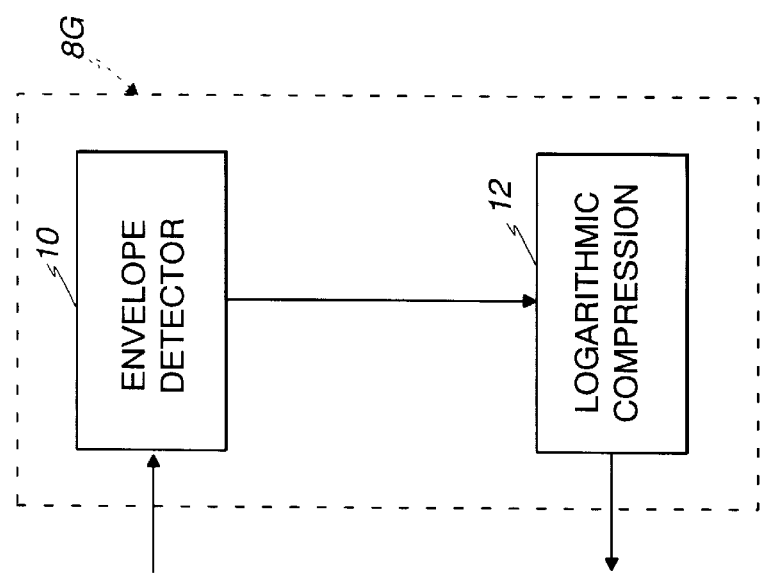
FIG. 3 is a schematic block diagram showing the mid processor B-mode apparatus illustrated in FIG. 1.

Referring to FIG. 3, gray scale B-mode mid-processor 8G includes an envelope detector 10 for forming the envelope of the beamsummed receive signal by computing the quantity $(I^2+Q^2)^{1/2}$. The envelope of the signal undergoes some additional B-mode processing, such as logarithmic compression (block 12 in FIG. 3), to form display data which is output to the scan converter 14 (FIG. 1).

Referring again to FIG. 1, the color flow estimates and gray scale display data are sent to the scan converter 14, which converts the data into X-Y format for video display. The scan-converted frames are passed to a video processor 16, which basically maps the video data to a display color map and gray scale image frames for video display. The image frames are then sent to the video monitor 18 for display. Typically, for color images, either velocity or power are displayed alone or velocity is displayed in conjunction with either power or turbulence. System control is centered in a host computer (not shown), which accepts operator inputs through an operator interface (e.g., a keyboard) and in turn controls the various subsystems.

In general, for B-mode gray scale images, the display data is converted by the scan converter 14 into X-Y format for video display. The scan-converted frames are passed to the video processor 16, which maps the video data to a gray scale or mapping for video display. The gray scale image frames are then sent to the video monitor 18 for display.

The images displayed by the video monitor 18 are produced from an image frame of data in which each datum indicates the intensity or brightness of a respective pixel in the display. An image frame may, e.g., comprise a 256×256 data array in which each intensity datum is an 8-bit binary number that indicates pixel brightness. The brightness of each pixel on the display monitor 18 is continuously refreshed by reading the value of its corresponding element in the data array in a well-known manner. Each pixel has an intensity value which is a function of the backscatter cross section of a respective sample volume in response to interrogating ultrasonic pulses and the gray map employed.

Figure 4:
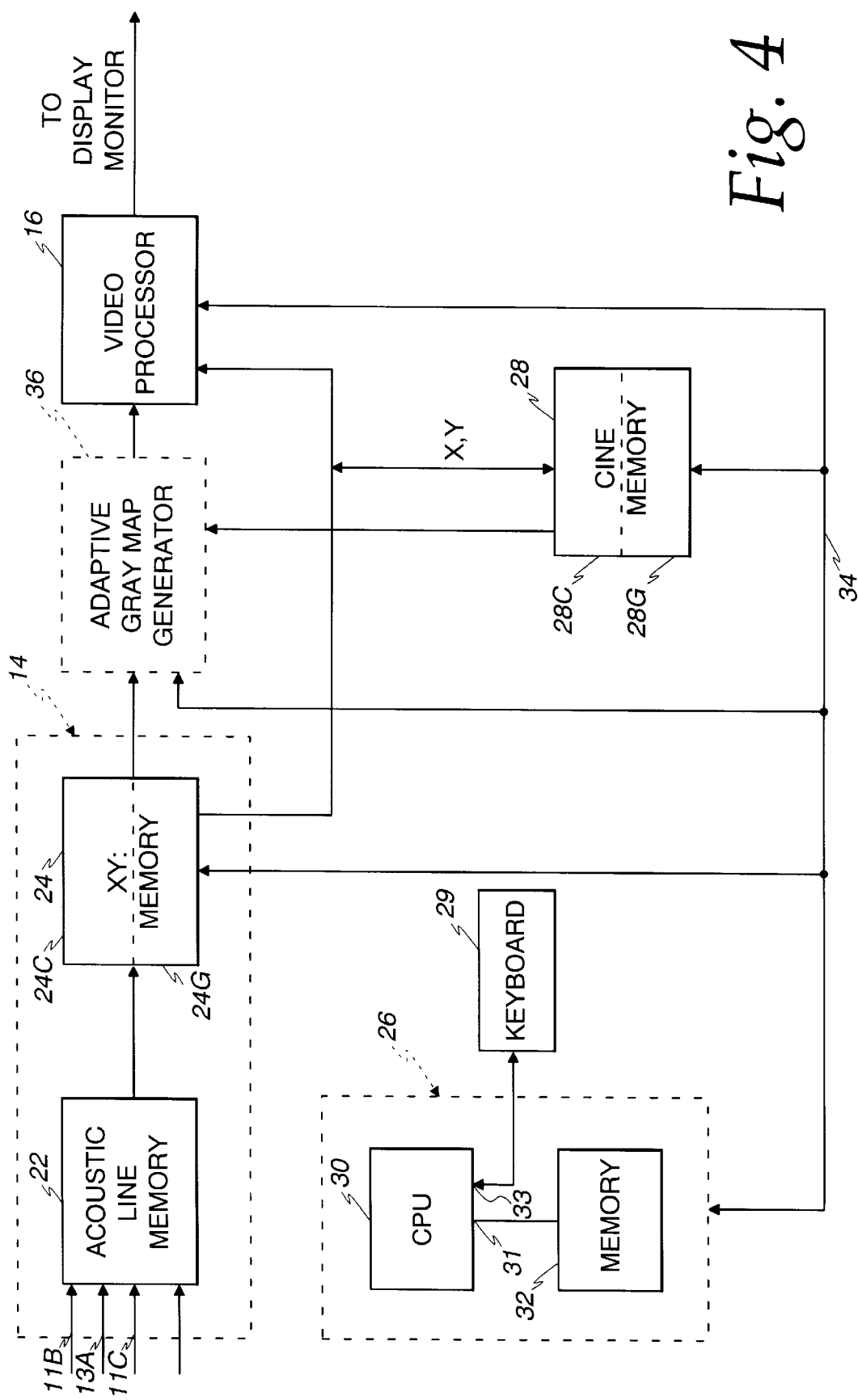
FIG. 4 is a schematic block diagram showing additional details of portions of the system illustrated in FIG. 1.

Referring to FIG. 4, system control is centered in a master controller or host computer 26, which accepts operator inputs through an operator interface (not shown) and in turn controls the various subsystems. The master controller 26 also generates the system timing and control signals. The master controller 26 comprises a central processing unit (CPU) 30 and a random access memory 32. A keyboard 29 is used to enter data into CPU 30. The CPU 30 has read only memory incorporated therein for storing routines used in constructing gray and color maps based on acquired raw data.

The scan converter 14 comprises an acoustic line memory 22 and an X-Y memory 24. The B-mode and color mode intensity data stored in polar coordinate (R-θ) sector format in acoustic line memory 22 is transformed Cartesian coordinate pixel display data, which is stored in X-Y memory 24. The color data is stored in memory locations 24C, and the gray scale data is stored in memory locations 24G. The scan-converted frames are passed to video processor 16, which maps the data to a gray map for video display. The gray scale image frames are then sent to the video monitor for display.

Successive frames of acoustic sample data are stored in cine memory 28 on a first-in, first-out basis. Color frames are stored in memory locations 28C, and gray scale frames arc stored in memory locations 28G. In the color region of interest, for every word of color data corresponding to a display pixel, there is a corresponding word of B-mode gray scale data corresponding to that pixel. The cine memory is like a circular image buffer that runs in the background, continually capturing acoustic sample data that is displayed in real time to the user. When the user freezes the system, the user has the capability to view acoustic sample data previously captured in cine memory.

The CPU 30 controls the XY memory 24 and the cine memory 28 via the system control bus 34. In particular, the CPU 30 controls the flow of raw data from the XY memory 24 to the video processor 16 and to the cine memory 28 and from the cine memory to the video processor 16 and to the CPU 26 itself. The CPU also loads the gray maps and color maps into the video processor.

Image frames are collected in cine memory 28 on a continuous basis. The cine memory 28 provides resident digital image storage for single image review and multiple image loop re view and various control functions. The region of interest displayed during single-image cine replay is that used during the image's acquisition. The cine memory also acts as a buffer for transfer of images to digital archival devices (not shown) via the master controller 26.

The CPU 30 has random access memory for storing routines used in acquiring a raw data histogram, determining the end points of a new gray map input range constructing a new gray map based on the end points of the new gray map input range, comparing the slope and gain of the new gray map to predetermined slope and gain limits, and if either limit is exceeded, reconstructing the new gray map to conform to the limit or limits.

In accordance with the preferred embodiments of the invention, the contrast of the ultrasound images is adjusted by the master controller 26 by creating a mapping of raw acoustic sample data into adjusted gray and color map values. First, the master controller 26 retrieves one or more image frames of raw data from the X-Y memory 24 or from the cine memory 28, storing that raw data in memory 32. The CPU 30 then compiles a histogram of the number of acoustic samples having an amplitude or value within each of a multiplicity of prescribed ranges or bins for the retrieved image frames of raw data.

According to the preferred embodiment, a color flow auto display processing mode is initiated by the user through keyboard 29 (FIG. 4) and can then be re-initiated by the user for updating of post-processing parameters or turned off altogether as the scanning situation changes.

The preferred embodiment uses the above-described B-mode gray scale and color flow scan data to optimize image quality of the color display. A composite histogram (histogram of the data over several frames) and/or a single frame histogram are constructed from the cine memory 28 data for color flow and/or B-mode by controller 26. Algorithms then are applied to the histogram results by controller 26 to determine how to properly adjust various parameters for a specific scanning situation or application.

Several algorithms are used to adjust various color flow display parameters. These algorithms are:

1. Auto Dynamic Range Selection Algorithm in color flow Power Doppler Imaging (PDI) Mode;
2. Auto B/Color Priority Threshold Selection Algorithm in the color flow Velocity and PDI Modes; and
3. Auto Color Map Threshold/Compression Algorithm in the color flow Velocity and PDI Modes.

The algorithms are described as follows:

Auto Dynamic Range Selection Algorithm In Color Flow Power Doppler Imaging (PDI) Mode By operating keyboard 29, the user may select the power only mode of color flow display (i.e., the PDI mode). According to the preferred embodiment, in the PDI mode, several discrete families of color flow dynamic range selections and data for corresponding compression curves are entered into memory 32 (FIG. 4). There is one family for each type of scanning application. For example, one family of dynamic range selections is used for ultrasound examination of the kidney, whereas another family of dynamic range selections is used for ultrasound examination of the carotid artery. In each family, there are three dynamic ranges available for automatic selection by the system. Each dynamic range is controlled by a different compression curve defined by digital data in memory 32.

The user enters the type of application on keyboard 29. In response, controller 26 presets the middle value dynamic range selection and corresponding compression curve which represents the typical dynamic range encountered when scanning the application selected by the user. The lower dynamic range in the family provides less dynamic range and the higher dynamic range in the family provides increased dynamic range compared to the middle dynamic range setting. Using the families of dynamic ranges, the auto dynamic range selection algorithm part of the auto color flow display processing mode automates dynamic range selection.

First, n frames of PDI color flow data are collected from cine memory 28C which represents the amplitude of the flow data present in the color flow region of interest (ROI) using the current preset dynamic range setting and compression curve. The n frames of data are required to account for flow pulsatility. Controller 26 executes the auto dynamic range selection algorithm which generates a first composite histogram of the data.

Figure 5:
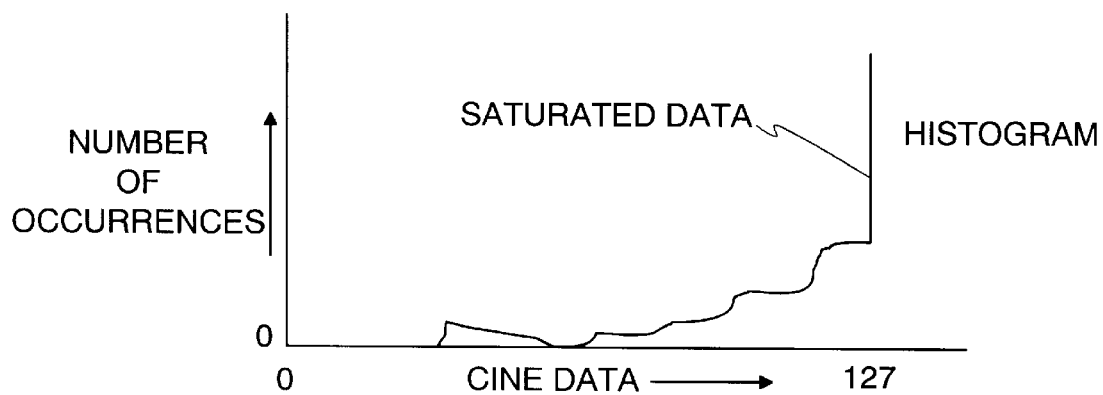
FIG. 5 is a graph illustrating one possible form of data stored in the cine memory shown in FIG. 4.

In the event the preset dynamic range is too low, a substantial percent of the data may be saturated at the maximum output value of 127. That is, the values are clustered in a range which is too high to create an optimum image on display monitor 18. Such a condition results in a first histogram of the type shown in FIG. 5. The auto dynamic range selection algorithm analyzes the first histogram, and, if at least x percent of the data is saturated at the maximum output value of 127 (i.e., condition 1 which is illustrated in FIG. 5), then the dynamic range is flagged as being too low, and the next higher dynamic range and corresponding compression curve stored in memory 32 are selected.

Figure 6:
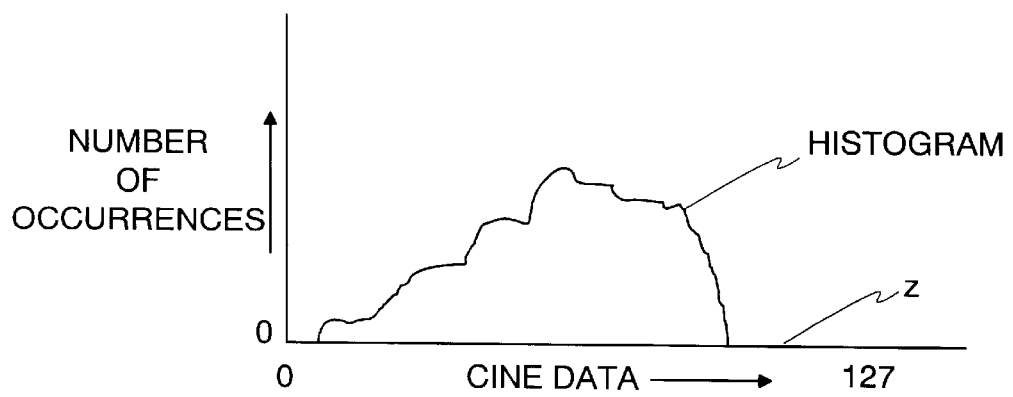
FIG. 6 is a graph showing another possible form of data stored in the cine memory shown in FIG. 4.

In the event the present dynamic range is too high, all of the data have values substantially below the maximum output value of 127. That is, all of the values are clustered in a range which is too low to create an optimum image on display monitor 18. Such a condition results in a first histogram of the type shown in FIG. 6. The auto dynamic range selection algorithm analyzes the first histogram, and, if less than t percent of the data occurs at output values between z and the maximum value of 127 (i.e., condition 2 which is illustrated in FIG. 6), then the dynamic range is flagged as being too high, and the next lower dynamic range and corresponding compression curve stored in memory 32 are selected.

Figure 7:
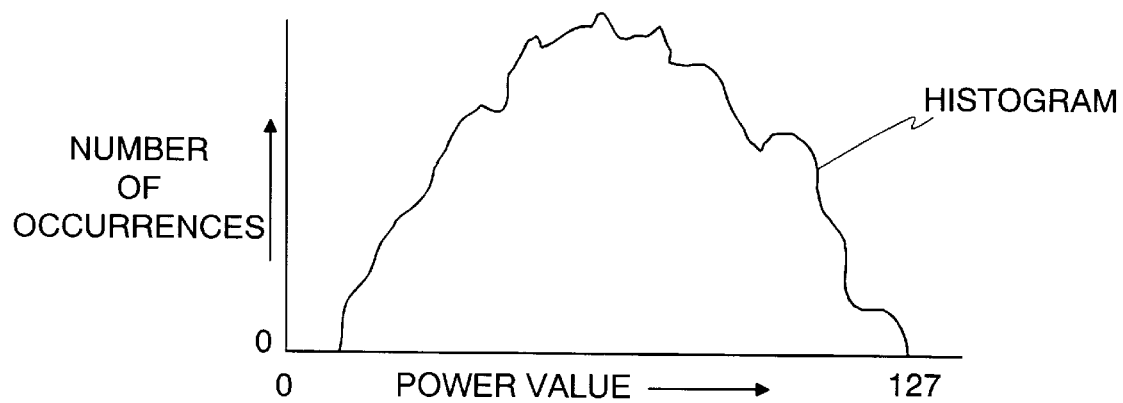
FIG. 7 is a graph showing yet another possible form of data stored in a memory illustrated in FIG. 4.

Based on the newly selected dynamic range and compression curve, the auto dynamic range selection algorithm calculates a second histogram based on the same data used to calculate the first histogram. The original dynamic range and compression curve are used to decompress the original data. The original data then is applied to the newly selected dynamic range and compression curve to create new compressed data in memory 32. The second histogram calculated from the new compressed data using the new dynamic range typically shows a spread of values more appropriate for optimum viewing on display monitor 18. Such an exemplary second histogram may be of the type shown in FIG. 7.

Alternatively, if more than three dynamic ranges and three compression curves per family are provided, the process may be repeated as new dynamic ranges and compression curves are selected. If the first histogram showed that the dynamic range was too low (i.e., condition 1 shown in FIG. 5), the process of selecting dynamic ranges and compression curves, decompressing the data, compressing the data using the newly selected curve and calculating second and subsequent histograms is repeated until y percent of the data or less is determined to be saturated (the condition shown in FIG. 7) or until the highest dynamic range setting is reached, effectively spreading the data out over more of the lower output values. If the original histogram showed that the dynamic range was too high (i.e., condition 2 shown in FIG. 6), the process of selecting dynamic ranges and compression curves, decompressing the data, compressing the data using the newly selected curve and calculating second and subsequent histograms is repeated until q percent of the data or more is determined to be between z and 127 (the condition shown in FIG. 7) or until the lowest dynamic range setting is reached, effectively spreading the data out over more of the higher output values.

As a second alternative, the first histogram may be used to calculate a new compression curve not previously stored which more nearly spreads the actual data over the dynamic range available for display. The new compression curve then is used to recompress the original data.

If neither condition 1 nor condition 2 is met, then the current dynamic rang e and compression curve are maintained.

As an alternative to the preceding steps, controller 26 forms a histogram of the PDI data before any dynamic range compression is applied or uncompresses the data and forms a histogram. Then the histogram of uncompressed PDI data is analyzed to determine its statistics, and an optimal dynamic range compression scheme is calculated. Various dynamic range compression curves such as logarithmic, cube root, S-curve, or others are optimally applied across the data based on the statistics of the histogram. This alternative preferably is implemented by a digital signal processor (DSP).

The user can choose to re-activate the color flow auto display processing mode, causing new data to be formed into a histogram, based on the current dynamic range setting, and causing the auto dynamic range selection algorithm to be re-employed. Or the user can turn off the color flow auto display processing mode, causing the current dynamic range setting to be maintained until the user changes the selection manually.

Auto B/Color Priority Threshold Selection Algorithm in Velocity and PDI Modes

By operating keyboard 29, the user may enter the color flow modes in which power and velocity data are used separately. In those modes, there is a B/color priority threshold which is user selectable from a softkey menu on keyboard 29 and which is preset to x % of the maximum B-mode gray scale value of 255. The threshold is received, for example, at terminals 31 and 33. For any pixel within the color mode region of interest (ROI), if the B-mode pixel value exceed s the selected B/color priority threshold, then the B-mode value is displayed for that pixel. Otherwise, the corresponding color pixel value is displayed, if there is one. The Auto B/Color Priority Threshold Selection Algorithm part of the Auto Color Flow Post Processing Mode works according to one of two methods:

The first method captures a single frame of B-mode data words from cine memory 28G and detects the n percent B-mode words having the largest values within the color ROI. For example, if n is 5 percent, then all the B-mode words of memory 28G in the color ROI are read, and the 5 percent of such words having the largest values are identified as a set. The B/Color priority threshold is then set to x percent of the mean of the set where x is the currently selected B/Color priority threshold percentage.

Figure 8:
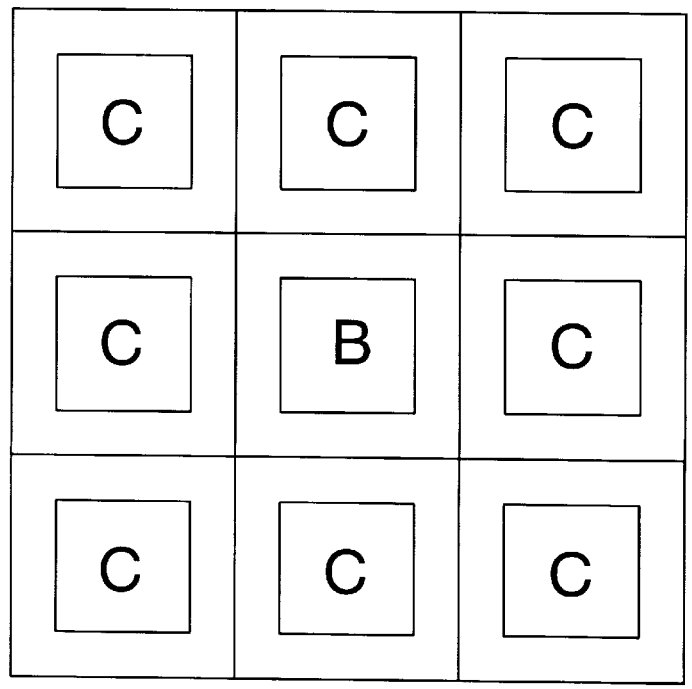
FIG. 8 is a schematic illustration of a window illustrating a method of data sampling in accordance with a preferred embodiment of the invention.

The second method captures N frames of B-mode data from cine memory 28G in the color ROI and N frames of color flow velocity or power data from cine memory 28c in the color ROI (depending on which mode the user is in). The number of nonzero occurrences of color flow pixels in each frame in the ROI is calculated. Then a single frame of color flow data along with its corresponding B-frame of data is selected from the N frames based on which color frame has the most total number of occurrences of color flow (nonzero) pixel data. The single B-frame of data and single color frame of data are then analyzed as follows:

An m-pixel by m-pixel filter is applied across the B/color 2-dimensional ROI data array formed by the frame of B-mode and frame of color mode data to determine the baseline number of B-mode "holes" in the image with an effective B/Color priority threshold of 100% applied. For example, a 3-pixel by 3-pixel filter would look for a single B pixel value surrounded by all color pixel values with the B/color priority threshold set to 100%. The threshold preferably is applied only to the B pixel value. This filter would be applied across the entire 2-dimensional ROI data and a single filtered result would appear as shown in FIG. 8 when a B-mode "hole" is present in the color flow data array.

When this filter is applied across the entire 13 mode and color data arrays using a B/color priority threshold of 100%, an initial or baseline count of the number of B-mode "holes" is established. Since the threshold is 100%, the baseline count is a minimum count. Then the B/color priority threshold is incrementally lowered, and the filter is again applied each time for each new B/color priority threshold, establishing a new count of the B-mode "holes". This process of lowering the threshold and establishing a new count is continued until the number of B-mode "holes" is some factor k greater than the minimum number of baseline B-mode "holes" in the baseline count. Factor k is preset differently as the user selects tissue type and flow type via keyboard 29. Preferably the baseline count at the 100% threshold is equal to or greater than 1. The factor k can be an offset or a multiple of the baseline count. Then this final B/color priority threshold is used to continue imaging. This process happens quickly enough that there is essentially no significant delay to the user.

At any time, the user can cause new data to be captured and the Auto B/Color Priority Threshold Selection Algorithm to be re-employed. Such reactivation is useful for new scanning conditions. Or the user can turn off the algorithm, causing the current B/color priority threshold to be maintained until the user manually changes the setting.

Auto Color Map Threshold/Compression Algorithm in Velocity and PDI Modes

The Auto Color Map Threshold /Compression Algorithm allows the stored map threshold to be reset for better detection of low velocity or low power flow and allows the map to be re-mapped or compressed over the range of color flow data actually present. Two algorithms are provided: one for velocity mode and one for PDI mode.

Figure 9:
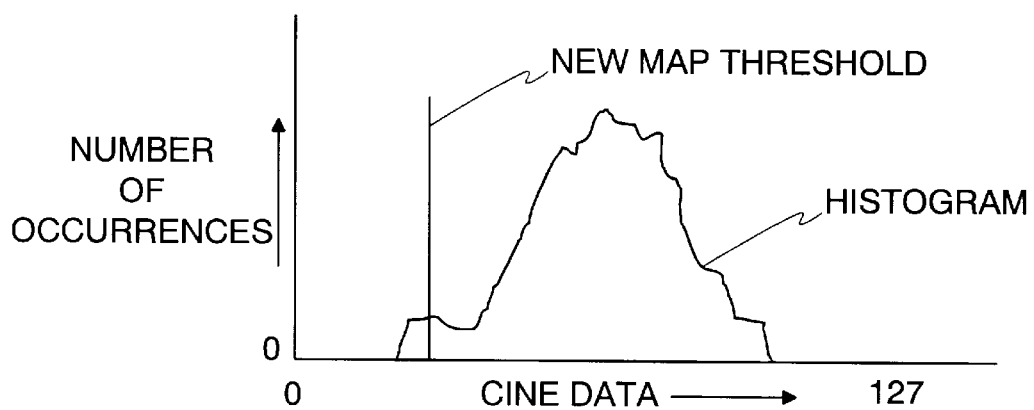
FIG. 9 and 10 are exemplary histograms formed in accordance with the preferred embodiment of the invention.

For velocity mode, N frames of color flow data are collected from cine memory 28C and formed into a composite histogram as shown in FIG. 9. The N frames are required to account for flow pulsatility. Then, the fixed map threshold is received by the algorithm from memory at a terminal 31 and is adjusted, if necessary, and the colormap is re-created to apply more colors of the map across the full range of data in the composite histogram. As FIG. 9 shows, the positive velocity data in the composite histogram does not cover the full range of 0 to 127, but instead covers some smaller range in-between.

The algorithm calculates the statistics of the histogram data and sets the new map threshold to be x standard deviations below the mean. The value of x is determined per application to maximize low velocity flow detection while minimizing low velocity artifacts such as residual wall or tissue motion. The negative map threshold similarly is set for negative velocities based on the statistics of the negative velocity histogram.

In this example of FIG. 9, the velocity color map is re-created (effectively compressed) to apply more of its colors across the range of data in the composite histogram, taking into account the map threshold as a reference end point.

Figure 10:
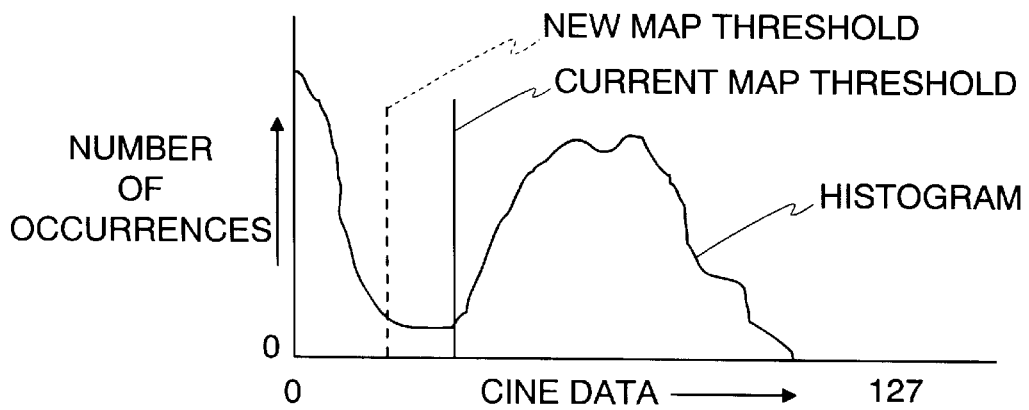

For the PDI mode, a second algorithm is employed. Again, a composite histogram is formed from the PDI data over N frames. The histogram of PDI data typically appears as shown in FIG. 10. This histogram may be the same one calculated in the Auto Dynamic Range Selection Algorithm previously described.

The histogram data is searched from the current map threshold setting and above to find the peak of the histogram data. Then the algorithm starts back at zero and searches for the bin where the histogram value first drops below the peak value previously found. An offset value is added to this bin value, and the new map threshold is set to this bin+ offset value.

For cases of opaque background PDI maps, the map threshold is fixed at zero and is not adjusted.

There are many ways to re-create the new color map once the composite histogram is known. One established technique is histogram equalization. This technique assumes that the current map has an end point at 0 and an end point at 127 (for PDI or positive velocity flow, or end points of 0 and −128 for negative velocity flow). Using the composite histogram, the algorithm determines new end points by searching for the end of the histogram from each direction (or using the newly established map threshold for the lower end point). Finally, the algorithm decimates the old map such that it is compressed between the newly established end points. This is the new map. Additional information about histogram equalization may be found in commonly assigned application Ser. No. 09/066150, filed Apr. 24, 1998, in the names of Washburn et al., entitled "Method And Apparatus For Ultrasound Imaging Using Adaptive Gray Mapping," bearing docket no. 15-UL-4660, which is incorporated by reference.

Referring to FIGS. 9 and 10, the algorithms may be varied as follows:

Rather than searching for the end points of the histogram from each direction, a pivot point can be established once x percent of the composite histogram data is found from one side. This enables a way to suppress the lowest y % of image data and the highest z % of image data. The end points can alternatively be established by calculating the standard deviation of the composite histogram data and defining the new end points with a particular number of standard deviations from the mean. There is no restriction that the same criteria be used at each end. Once the end points are established, it is possible that they are so close that the resulting color map will make the image difficult to perceive. Therefore, it is useful to establish practical limits on how much the new map will be compressed, essentially backing off on the end points to prevent an undesirable map.

The new map also may display the center of the histogram at a dramatically different color level than the old map. Therefore, the end points can also be manipulated so that the resulting color change is within a defined limit.

The algorithm described here decimates the old map to fit between the new end points. It is also possible to generate an entirely new map between the end points rather than basing it on the old map. However, retaining the characteristics of the original map has the added advantage of maintaining any subjective aesthetic user-preference for the current map.

The embodiments described here can be extended to automatically adjust other post-processing parameters such as power thresholds, wall filter cutoffs, baseline shifts, and velocity scales. The same basic idea of collecting B and/or color flow frames of cine data would be applied and associated algorithms would be employed to determine exactly how to adjust the particular post processing parameter.

The foregoing preferred embodiments have been disclosed for the purpose of illustration. Variations and modifications of the concept of the invention will be readily apparent to persons skilled in the art. All such variations and modifications are intended to be encompassed by the claims set forth hereinafter.

What is claimed is:

1. In an ultrasound imaging system generating color flow signals in response to ultrasound signals backscattered from a subject under study and generating image signals based on the amplitude of ultrasound signals backscattered from the subject under study, improved apparatus for displaying images in response to the color flow signals comprising in combination:

a terminal connected to receive a first threshold signal having a first threshold value and a second threshold signal having a second threshold value;

a memory connected to store a first set of data words in response to the color flow signals and a second set of data words in response to the image signals;

a logic unit connected to determine a dynamic range compression scheme based on an analysis of the data words in the first set, to alter the data words in the first set based on the determined dynamic range compression scheme, to alter the second threshold value based on an analysis of the first set of data words, to determine a characteristic value corresponding to at least one characteristic of the second set of data words, to alter the first threshold value in response to the characteristic value and to select data words from the first and second sets depending on a first predetermined relationship between the altered first threshold value and altered second threshold value and the values of the data words in the first and second sets; and a display connected to display a color flow image in response to the selected data words.

2. Apparatus, as claimed in claim 1, wherein the logic unit is connected to create the dynamic range compression scheme based on an algorithm which analyzes the first set of data words.

3. Apparatus, as claimed in claim 1, wherein the memory is connected to store compression data defining first and second dynamic range compression schemes, wherein the logic unit determines the dynamic range compression scheme by selecting one of the first or second stored dynamic range compression schemes and wherein the first set of data words are altered based on the selected dynamic range compression scheme.

4. Apparatus, as claimed in claim 3, wherein the logic unit is connected to analyze the data words in the first set by decompressing the data words in the first set, analyzing the decompressed data words, selecting one of the first or second stored dynamic range compression schemes, altering the decompressed data words based on the selected dynamic range compression scheme and enabling storage of the altered data words.

5. Apparatus, as claimed in claim 1, wherein the memory stores a color map and wherein the logic unit is connected to alter the color map based on analyzing the first set of data words.

6. Apparatus, as claimed in claim 5, wherein the memory is connected to store a color map and wherein the logic unit is connected to alter the values of the color map based on a compression scheme determined by locating end points of the histogram.

7. Apparatus, as claimed in claim 1, wherein the logic unit is connected to analyze the data words in the first set by generating a histogram of the values of the data words in the first set.

8. Apparatus, as claimed in claim 7, wherein the memory is connected to store a color map and wherein the logic unit is connected to alter the color map based on equalization of the histogram.

9. Apparatus, as claimed in claim 1, wherein at least some of the data words in the first set represent power estimates calculated in response to the backscattered signals.

10. Apparatus, as claimed in claim 1, wherein at least some of the data words in the first set represent velocity estimates calculated in response to the backscattered signals.

11. Apparatus, as claimed in claim 1, wherein the image signals comprise B-mode signals.

12. Apparatus, as claimed in claim 1, wherein the one characteristic comprises the mean of the values of the data words in at least a portion of the second set.

13. Apparatus, as claimed in claim 12, wherein the portion of the second set comprises a predetermined percentage of the data words in the second set having the largest values.

14. Apparatus, as claimed in claim 1, wherein the first predetermined relationship results in selection of a data word in the second set if the value of the data word in the second set compares to the altered first threshold value in a predetermined manner and selection of a data word in the first set if the value of the data word in the second set fails to compare to the altered first threshold value in the predetermined manner.

15. Apparatus, as claimed in claim 14, wherein the additional threshold values are less than the initial threshold value.

16. Apparatus, as claimed in claim 15, wherein the fourth predetermined relationship comprises one or more words from the second set which when displayed are surrounded by images resulting from data words from the first set.

17. Apparatus, as claimed in claim 15, wherein the second predetermined relationship comprises data words having values exceeding the initial threshold value.

18. Apparatus, as claimed in claim 14, wherein each of the samples comprises one or more data words from the second set having a fourth predetermined relationship with respect to corresponding data words from the first set.

19. Apparatus, as claimed in claim 1, wherein the logic unit is connected to determine the characteristic value by setting the first threshold value to an initial threshold value, analyzing samples of the second set of data words to determine an initial count of data words in the second set having a second predetermined relationship with respect to the initial threshold value, adjusting the initial threshold signal to one or more additional threshold values, analyzing samples of the second set of data words one or more additional times until the number of second set data words having the second predetermined relationship with respect to the additional threshold values reaches a target count having a third predetermined relationship with respect to the initial count and corresponding to a target threshold value, and setting the first threshold value equal to the target threshold value.

20. Apparatus, as claimed in claim 19, wherein the third predetermined relationship comprises a target count which is a multiple of the initial count.

21. In an ultrasound imaging system generating color flow signals in response to ultrasound signals backscattered from a subject under study and generating image signals based on the amplitude of ultrasound signals backscattered from the subject under study, an improved method for displaying images in response to the color flow signals comprising the steps of:

receiving a first threshold signal having a first threshold value;

receiving a second threshold signal having a second threshold value;

storing a first set of data words in response to the color flow signals and a second set of data words in response to the image signals;

determining a dynamic range compression scheme by analyzing the data words in the first set;

altering the data words in the first set based on the determined dynamic range compression scheme;

altering the second threshold value based on an analysis of the first set of data words;

determining a characteristic value corresponding to at least one characteristic of the second set of data words;

altering the first threshold value in response to the characteristic value;

selecting data words from the first and second sets depending on a first predetermined relationship between the altered first threshold value and altered second threshold value and the values of the data words in the first and second sets; and displaying a color flow image in response to the selected data words.

22. A method, as claimed in claim 21, wherein the step of determining a dynamic range comprises the step of creating the dynamic range compression scheme.

23. A method, as claimed in claim 21, wherein the step of storing comprises the step of storing compression data defining first and second dynamic range compression schemes, and wherein the step of determining a dynamic range compression scheme comprises the step of selecting one of the first or second stored dynamic range compression schemes and wherein the step of altering the data words in the first set comprises the step of altering based on the selected dynamic range compression scheme.

24. A method, as claimed in claim 23, wherein the step of altering the data words in the first set comprises the steps of:

decompressing the data words in the first set;

analyzing the decompressed data words;

selecting one of the first or second stored dynamic range compression schemes;

altering the decompressed data words based on the selected dynamic range compression scheme; and storing the altered data words.

25. A method, as claimed in claim 21, wherein the step of storing comprises the step of storing a color map and wherein the step of displaying comprises the step of altering the color map based on the analyzing of the data words in the first set.

26. A method, as claimed in claim 21, wherein the step of analyzing comprises the step of analyzing the data words in the first set by generating a histogram of the values of the data words in the first set.

27. A method, as claimed in claim 26, wherein the step of storing comprises the step of storing a color map and wherein the step of displaying comprises the step of altering the color map based on equalization of the histogram.

28. A method, as claimed in claim 26, wherein the step of storing comprises the step of storing a color map and wherein the step of displaying comprises the step of altering the color map based on a compression scheme determined by locating end points of the histogram.

29. A method, as claimed in claim 21, wherein at least some of the data words in the first set represent power estimates calculated in response to the backscattered signals.

30. A method, as claimed in claim 21, wherein at least some of the data words in the first set represent velocity estimates calculated in response to the backscattered signals.

31. A method, as claimed in claim 21, wherein the image signals comprise B-mode signals.

32. A method, as claimed in claim 21, wherein the one characteristic comprises the mean of the values of the data words in at least a portion of the second set.

33. A method, as claimed in claim 32, wherein the portion of the second set comprises a predetermined percentage of the data words in the second set having the largest values.

34. A method, as claimed in claim 21, wherein the first predetermined relationship results in selection of a data word in the second set if the value of the data word in the second set compares to the altered first threshold value in a predetermined manner and results in selection of a data word in the first set if the value of the data word in the second set fails to compare to the altered first threshold value in the predetermined manner.

35. A method, as claimed in claim 21, wherein the step of determining the characteristic value comprises the steps of:

setting the first threshold value to an initial threshold value;

analyzing samples of the second set of data words to determine an initial count of data words in the second set having a second predetermined relationship with respect to the initial threshold value;

adjusting the initial threshold signal to one or more additional threshold values;

analyzing samples of the second set of data words one or more additional times until the number of second set data words having the second predetermined relationship with respect to the additional threshold values reaches a target count having a third predetermined relationship with respect to the initial count and corresponding to a target threshold value; and setting the first threshold value equal to the target threshold value.

36. A method, as claimed in claim 35, wherein the additional threshold values are less than the initial threshold value.

37. A method, as claimed in claim 35, wherein each of the samples comprises one or more data words from the second set having a fourth predetermined relationship with respect to corresponding data words from the first set.

38. A method, as claimed in claim 37, wherein the fourth predetermined relationship comprises one or more words from the second set which when displayed are surrounded by images resulting from data words from the first set.

39. A method, as claimed in claim 35, wherein the second predetermined relationship comprises data words having values exceeding the initial threshold value.

40. A method, as claimed in claim 35, wherein the third predetermined relationship comprises a target count which is a multiple of the initial count.

* * * * *